(12) United States Patent
Fischer

(10) Patent No.: US 6,283,946 B1
(45) Date of Patent: Sep. 4, 2001

(54) LONG STEM SYRINGE APPARATUS FOR DISPENSING COMPOSITIONS AND RELATED METHODS

(75) Inventor: Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/455,552

(22) Filed: Dec. 6, 1999

(51) Int. Cl.[7] ............................. A61M 5/315; A61M 5/00
(52) U.S. Cl. ................................. 604/218; 604/235
(58) Field of Search ........................... 604/187, 191, 604/207, 208, 218, 220, 221, 225, 227–229, 235; D24/112, 113

(56) References Cited

U.S. PATENT DOCUMENTS

| | | | |
|---|---|---|---|
| D. 322,317 | 12/1991 | Fischer | D24/130 |
| 1,277,445 | * 9/1918 | MacGregor | 128/223 |
| 3,780,735 | * 12/1973 | Crouter et al. | 128/223 |
| 4,925,449 | * 5/1990 | Saez et al. | 604/227 |
| 4,986,820 | 1/1991 | Fischer | 604/218 |
| 5,078,690 | * 1/1992 | Ryan | 604/187 |
| 5,290,259 | 3/1994 | Fischer | 604/218 |
| 5,328,462 | 7/1994 | Fischer | 604/82 |
| 5,334,156 | * 8/1994 | Serrano Gonzalez | 604/110 |
| 5,665,066 | 9/1997 | Fischer | 604/82 |
| 5,697,903 | 12/1997 | Fischer | 604/82 |
| 5,697,918 | * 12/1997 | Fischer et al. | 604/227 |
| 6,135,984 | * 10/2000 | Dishler | 604/267 |

* cited by examiner

*Primary Examiner*—Sharon Kennedy
(74) *Attorney, Agent, or Firm*—Workman, Nydegger & Seeley

(57) ABSTRACT

A syringe is provided for delivering compositions while holding the syringe in only one grasping position. The syringe has a hollow elongated barrel engaged by a plunger which have unique relative lengths. The plunger has a length that is sufficiently longer than that of the chamber of the barrel to enable a user to grasp the syringe in a single position and to then continuously deliver a composition from the chamber by advancing the plunger within the chamber until the composition is expressed from the chamber. The plunger is preferably twice as long as the chamber such that when the plunger is fully advanced within the chamber a portion of the plunger extends out of the chamber with a length that is at least equal to that of the chamber. Using only one grasping position enables the syringe to be used to continuously deliver a composition, thereby eliminating the possibility of accidentally moving the syringe due to altering one's grasp of the syringe or the possibility of suddenly varying the delivery rate. The syringes are particularly useful with dental compositions especially two part compositions.

41 Claims, 8 Drawing Sheets

LONG STEM SYRINGE APPARATUS FOR DISPENSING COMPOSITIONS AND RELATED METHODS

BACKGROUND OF THE INVENTION

1. The Field of the Invention

The present invention relates to a syringe apparatus for dispensing compositions such as dental cements. More particularly, the present invention is directed to syringes which enable compositions to be delivered without requiring significant exertion and preferably in relatively small quantities.

2. The Relevant Technology

An example of a widely used conventional syringe is shown in FIGS. 1A–1D at 10. Syringe 10 is shown having a barrel 20 with a plunger 50 slidably engaged therein. In order to appreciate certain limitations of syringes such as syringe 10, it is necessary to understand the details of the elements of such a syringe. These elements are briefly described hereinbelow.

Barrel 20 has a top grasping end 21 opposite a bottom end 29 with a substantially cylindrical sidewall 22 extending therebetween. Sidewall 22 has an exterior surface 23 and an interior surface 24. Interior surface 24 defines a substantially cylindrical chamber 25 for holding a composition. Chambers such as chamber 25 of barrel 20 are typically configured to hold about 1.2 cc of liquid.

Barrel 20 has a grasping handle 26 which is an annular flange extending radially outward from sidewall 22 at top grasping end 21 of barrel 20. Grasping handle 26 is centrally located around opening 27 which has the same diameter as the interior surface 24 of chamber 25.

A radial extension 28 extends integrally from sidewall 22 at bottom end 29 inward to define an exit port 32. Radial extension 28 acts as a stop for plunger 50 as plunger 50 is depressed.

Exit port 32 is the opening into channel 33 which enables channel 33 to communicate with chamber 25. Note that channel 33 is the interior surface of tapered exit tube 30. Channel 33 extends through tapered exit tube 30 and terminates at outlet 34.

Surrounding exit tube 30 is an attachment sleeve 36. Attachment sleeve 36 has an interior surface 37 with engagement threads 38 positioned thereon. A nozzle or tip 40, shown in FIGS. 1C and 1D, may be selectively attached to barrel 20 by coupling with threads 38. A variety of tips are available which may be attached such that channel 33 of exit tube 30 is in fluid communication with the tip for guided delivery of the composition to a desired location.

Tip 40 is configured to selectively attach in fluid communication with exit tube 30. To accomplish this end, tip 40 has a threaded end 42 for engagement with threads 38 of attachment sleeve 36. Opposite threaded end 42 is a flexible and angled spout 44 for guiding delivery of the composition to a desired location. It is of course envisioned that different sizes and shapes of spouts 44 can be used depending on the type and intended use of the composition. Furthermore, in alternative embodiments, tip 40 may be permanently attached to bottom end 29 or means other than threads may be used to attach different sizes and/or shapes of tips.

Plunger 50 has a distal lead end 51 opposite from a proximal pushing end 53 with a stem 52 extending therebetween. Radially extending outward at pushing end 53 is an annular pushing handle 58 used in advancing plunger 50. Plunger 50 is sized to be slidably received within chamber 25 through opening 27 at top grasping end 21. Plunger 50 has a length that permits it to be advanced to bottom end 29 such that a small portion of plunger 50 remains extending beyond opening 27.

Positioned at lead end 51 of plunger 50 is a cylindrically shaped sealing gasket 60. More particularly, gasket 60 is coupled to stem 52 via a gasket holder as shown in FIG. 1B at 64. Gasket 60 is made of a soft, compressible, sealing material, such as rubber, which allows the exterior surface of gasket 60 to seal against interior surface 24 of chamber 25 as plunger 50 is advanced within chamber 25 or selectively slid down to bottom end 29. Gasket holder 64 has a post 66 with a head element 65 integrally extending at one end and a base 67 integrally extending from the other end. Head element 65 and post 66 are inserted into an opening 62 of gasket 60 which expands such that head element 65 can be inserted therein and then elastically return to its original size such that head element 65 is removably held in gasket 60. Base 67 is connected to stem 52 to hold gasket holder 64 in position.

As discussed above, a small portion of plunger 50 remains extending beyond opening 27, as shown in FIG. 1D, when plunger 50 has been fully depressed such that gasket 60 contacts radial extension 28. The length of the portion of plunger 50 extending beyond opening 27 of syringe 10 when plunger 50 is fully depressed is about 1 cm. This configuration is typical for a conventional 1.2 cc syringe. Note that the length of the barrel is about 5 cm while the length of the plunger which includes gasket 60 is about 6 cm such that the ratio of the length of the plunger to the length of the chamber is 1.2:1.

While syringes such as syringe 10 are ideal for many uses, these syringes also have certain limitations. For example, in some instances it can be difficult to apply an adequate amount or the appropriate amount of force required to push the composition from chamber 25 into channel 33 and ultimately out of tip 40 attached to barrel 20. FIG. 1C depicts a loaded syringe with only gasket 60 and a portion of stem 52 in chamber 25 of barrel 20. As shown in FIG. 1C, a user typically grasps syringe 10 such that barrel 20 is held by the user's middle and index fingers as well as the user's thumb. As the plunger is depressed further and further into chamber 25 until gasket 60 contacts radial extension 28 to stop the depression of plunger 50 as shown in FIG. 1D, the user may have to exert increasing effort to dispense the composition. Accordingly, it becomes difficult to dispense the composition at a uniform rate and in a controlled manner. When a composition is relatively viscous, the difficulty experienced in applying either an adequate amount or the appropriate amount of force may further increase.

When an inappropriate amount of force is applied to pushing handle 58, gasket 60 may press against sidewall 22 of chamber 25 in a manner such that plunger 50 is not smoothly pushed into chamber 25 in a controlled manner. Plunger 50 may stop and then suddenly move downward in what is known as a stuttering effect. This can potentially result in delivery of excessive amounts of a composition which the practioner is attempting to deliver in a discrete amount.

Syringes such as syringe 10 are used for delivering many different types of compositions. Such syringes may be sold with preloaded compositions ready for immediate use. However, when it is necessary to deliver a two part composition having an A component and a B component which are mixed just before use, other syringes are typically utilized.

Upon mixing a formulation packaged in two parts, including A and B components, the A and B components typically undergo a chemical reaction which causes the resultant composition to "set up" in some desired manner. Such two part compositions are widely used in the dental field. For example, glass ionomer cements and resinous luting cements are frequently used for applications such as securing dental crowns in place. Temporary cements are also provided as two separate components which are mixed shortly before delivery. Also, some dental impressions are made using compositions of A and B components.

In order to work properly, it is important that the A and B components of these multi-component compositions be mixed together rapidly and thoroughly and in the right proportions. Failure to rapidly mix the components can result in loss of valuable working time due to the quick setting nature of the compositions. Furthermore, failure to rapidly mix the components can result in a non-homogenous composition due to uneven setting of the composition. Poorly mixed compositions can have less than optimum characteristics. For example, if a poorly mixed composition is used as a cement, it is possible that portions of the cement will fail to reach the chemical strength required for a long-term bond.

Problems of obtaining rapid and uniform mixing are often complicated by differences in the A and B components. Sometimes it is necessary to mix two liquids, while other times it is necessary to mix a powder with a liquid. Sometimes there are equal amounts of the A and B components, but other times there is more of one component than another. Sometimes the two components have similar viscosities, while at other times the two components have widely differing viscosities.

A syringe system for mixing two part compositions or A/B compositions is disclosed in U.S. Pat. No. 5,328,462 which issued to Dan E. Fischer and is owned by Ultradent Products, Inc. U.S. Pat. No. 5,328,462 is hereby incorporated by reference. An example of a syringe as disclosed in U.S. Pat. No. 5,328,462 is depicted in FIG. 2 of the present document at 10'. Note that the only difference between syringe 10 and syringe 10' is that barrel 20' has a vent hole 15 for venting air when plunger 50 is inserted into syringe barrel 20' after mixing.

U.S. Pat. No. 5,328,462 also discloses that the most effective mixing is achieved by delivering the components in a side-by-side fashion instead of one on top of the other. Such side-by-side loading is achieved through the use of a two-syringe device as disclosed in U.S. Pat. No. 5,328,462 and also in U.S. Pat. No. 5,290,259, which is also incorporated by reference. U.S. Pat. No. 5,290,259 also issued to Dan E. Fischer and is owned by Ultradent Products Inc. An example of a two-syringe device as detailed in these patents is shown in FIG. 3 at 110 with two syringe barrels at 120a and 120b. The output ends of syringe barrels 120a and 120b are fitted with tips 140a and 140b. Tips 140a and 140b are adapted at one end to be secured to the syringe barrels. The other end of each tips is adapted to be secured to a tubing members. Tubing members 146a and 146b are configured for delivering the two components into a syringe barrel such as barrel 50'. A collar 148 holds tubing members 146a and 146b together.

Prior to use, the syringe barrels 120a and 120b are filled with A and B components, respectively, of a two-component composition. The two plungers 150a and 150b are then simultaneously depressed while slowly withdrawing tubing members 146a and 146b from within the chamber of the barrel. This results in placement of material from each of syringe barrels side-by-side within the chamber.

After the two components have been delivered into syringe barrel 50' through the use of two-syringe device 110, it is necessary to mix the two components together. U.S. Pat. No. 5,328,462, which is referenced above, discloses various mixer elements for mixing the two components, an example of which is depicted in FIG. 4 at 170 in this document. Mixer element 170 also referred to as a spatula or paddle is inserted into barrel 50' and rotated until the two components are thoroughly mixed together. Other mixer elements are also disclosed in U.S. Pat. No. 5,697,903 which issued to Dan E. Fischer and is owned by Ultradent Products, Inc. U.S. Pat. No. 5,697,903, is hereby incorporated by reference.

Note that as stated in U.S. Pat. No. 5,328,462 at column 3, line 55 to column 4, line 10, the location of the vent hole limits the volume of material which can be dispensed from syringe 10'. If the vent hole is too high then air may be trapped and if it is too low then the composition may leak out of the vent hole. So the composition cannot be delivered into the barrel above the vent hole. Note that the structure of the barrel above the vent hole is resultingly utilized only to guide the plunger and not to hold a composition.

U.S. Pat. No. 5,665,066, which issued to Dan E. Fischer and is owned by Ultradent Products, Inc. discloses a configuration for avoiding the use of a vent hole in the barrel. U.S. Pat. No. 5,665,066, which is hereby incorporated by reference, discloses the use of a cylindrically shaped sealing gasket such as that shown at 60 which has a vent hole. The vented sealing gasket, which is referred to in U.S. Pat. No. 5,665,066 as a piston, is shown in FIG. 5 at 60". The vent hole of sealing gasket 60" is identified at 62". As shown in FIG. 5, the vented sealing gasket is pushed down toward the composition 90 to enable air to be released by pushing on the top surface 61" of gasket 60" with the distal end 56" of taper tip 54" of plunger 50". Once the composition is contacted by the bottom surface 68" of vented sealing gasket 60", distal end 56" of taper tip 54" of plunger 50" is inserted into vent hole 62" and plunger 50" is depressed against composition 90 to express the composition out of the syringe. A disadvantage of this system is that it is difficult to depress the vented sealing gasket very far into the barrel with plunger 50" so it is necessary to fill the barrel with as much of the composition as possible. Naturally, as more composition is delivered into the barrel the potential increases for incorporating air which must subsequently be released.

One problem associated with the delivery of two-part compositions with a two-syringe device as shown in FIG. 3 at 110 into a barrel such as barrel 50, 50', and 50" is that air may be introduced into the barrel due to the inability or failure of the ends of tubing members 146a and 146b to reach the bottom end of the barrel. The length of the tubing members can be increased but this also increases the amount of pressure required to deliver the components.

Undesired air bubbles can be introduced into the composition at various stages. During the mixing process, the stirring action of the spatula or similar mixing instrument, can introduce and cause air bubbles to be entrapped or entrained within the mixed composition. Furthermore, as mentioned above, transferring the mixed composition to a syringe can also cause air to become entrained within the composition. Depending on the composition and its intended use, the presence of air bubbles can have a detrimental affect. For example, when cements are used in the dental field, such as in bonding dental crowns, air bubbles in the composition can result in uneven layering or placement of the cement. In turn, the crown may not be uniformly secured and thus have a weaker long term bond. The presence of air bubbles can also effect the setting rate of the composition. That is, the portion of the composition exposed to the air bubbles may begin setting quicker than the remaining portion of the composition. This uneven setting can also influence the resulting effectiveness of the composition.

Another solution to the problems resulting from the introduction of air is presented in U.S. Pat. No. 5,697,903 which is referenced above. U.S. Pat. No. 5,697,903 discloses a syringe such as the syringe shown at 10''' in FIG. 6. Syringe 10'' has a barrel 50''' with an access port 17. FIGS. 6 depicts access port 17 being utilized in conjunction with two-syringe device 110 to deliver a two part composition into chamber 25'''. More specifically, tubing members 146a and 146b of two-syringe device 110 are shown extending into chamber 25''' to deliver the two part composition.

Access port 17 of syringe 10''' allows tubing members 146a and 146b to be shorter than when tubing members 146a and 146b must reach through opening 27 of syringe 10, 10' or 10'' toward the bottom end of the barrel. As a result, less effort is required to deliver the two components into the barrel. Additionally, the tubing members can reach the radial extension of syringe 10''' and then begin filling as opposed to merely extending into the barrel as with the other syringes. Once tubing members 146a and 146b have contacted the radial extension and the two components have begun flowing, the tubing members can be withdrawn as the two components are laid down side by side until reaching a demarcation line shown at 19.

The side-ported syringe structure and associated methodology disclosed in U.S. Pat. No. 5,697,903 enables a syringe such as syringe 10''' to be very useful for minimizing the introduction of air into the composition. However, such a side-ported syringe also requires that all of the structure of the barrel above access port 17, more particularly above demarcation line 19, is used to guide the plunger and not to hold a composition.

In conclusion, a syringe is needed which enables a user to deliver a composition in a highly controlled manner. What is also needed in the art is a syringe which minimizes the entrainment of air when filled, especially with two component compositions. Additionally, such a syringe is needed which also minimizes plastic usage through minimizing the portion of the syringe barrel which merely guides the plunger and does not hold a composition.

OBJECTS AND BRIEF SUMMARY OF THE INVENTION

Accordingly, it is a primary object of the present invention to provide improved methods and apparatus for dispensing compositions.

Another object of the present invention is to provide methods and apparatus for enabling a practioner to exert essentially the same amount of effort and appropriate amounts of pressure throughout the entire depression of the plunger into the barrel.

Yet another object of the present invention is to provide methods and apparatus for enabling a practioner to easily apply adequate amounts of pressure to dispense a composition as desired without regrasping the syringe during the depression of the plunger into the barrel.

A further object of the present invention is to provide methods and apparatus for enabling a practioner to dispense compositions in small quantities so as to avoid waste.

An additional object of the present invention is to provide improved methods and apparatus for dispensing and mixing multi-component compositions which effect rapid and thorough mixing directly in the syringe and yet does not require any subsequent venting and results in a mixed composition which is essentially free from entrained air.

Finally, an object of the present invention is to provide improved methods and apparatus for dispensing compositions which enable a user to grasp a syringe in a single position such that the syringe is not moved relative to a delivery site during the delivery of the composition to the delivery site due to movement of the users hand.

Additional objects and advantages of the invention are set forth hereinbelow in the detailed description, or will be appreciated by the practice of the invention.

To achieve the foregoing objects, and in accordance with the invention as embodied and broadly described herein, the present invention provides a novel syringe having an a hollow elongated barrel engaged by a plunger which have unique relative lengths.

The barrel has a sidewall extending between a top grasping end and an opposing bottom end. The sidewall has an interior surface which defines a chamber for holding a composition. The barrel also has an opening at the top grasping end for accessing the chamber and an exit port at the bottom end for enabling the composition to exit the chamber. A grasping handle which extends perpendicularly and radially from the sidewall is located at the proximal grasping end of the barrel.

The plunger is positioned within the chamber of the barrel to advance the composition positioned within the barrel through the exit port at the bottom end of the barrel. The plunger has a distal lead end opposite from a proximal pushing end.

In contrast to prior art syringes which have chambers and plungers with approximately the same lengths, the plunger has a length that is significantly longer than that of the chamber of the barrel. The plunger preferably has a length that is at least twice that of the chamber of the barrel. Accordingly, when the plunger is fully advanced within the chamber a portion of the plunger extends out of the chamber with a length that is preferably at least equal to that of the chamber.

The above described syringe and method of use provides several advantages and improvements over the prior art. The length of the plunger relative to that of chamber enables the syringe to be grasped in a single position and then to be used to continuously deliver the composition by advancing the plunger within the chamber until the composition is expressed from the chamber. This is a significant advantage as it eliminates the possibility of accidentally moving the syringe due to altering one's grasp of the syringe. It is typically necessary to regrasp prior art syringes as the plunger is depressed within the barrel. Not only is it unnecessary to regrasp the syringe during the depression of the plunger into the chamber, the configuration of the syringe also enables a user to exert less effort in delivering the composition. Further, the configuration enables a user to exert essentially the same amount effort throughout the depression of the plunger within the chamber of the barrel, thereby avoiding the possibility of suddenly varying the delivery rate.

The syringes can be used with any composition, however, such plungers are particularly usefull with dental compositions especially two part compositions. The chamber is preferably sized to hold just enough composition for use in a single dental restorative procedure. The relative shortness of the chamber enables two part compositions to be easily delivered into the chamber as two-syringe devices can reach the bottom of the chamber. The composition is initially deposited at the bottom of the chamber and is then continuously deposited while subsequently moving the two-syringe device away from the bottom of the chamber. This enables the entrainment of air during delivery of the two part compositions into the chamber to be minimized. As a result, it is not necessary for either the chamber or the plunger to be vented. Additionally, it is not necessary to have a side port for delivering the composition into the chamber. This also enables less plastic material to be used for the chamber which merely guides the plunger and does not hold a composition.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained will be understood, a more particular description of the invention briefly described above will be rendered by reference to a specific embodiment hereof which is illustrated in the appended drawings. Understanding that these drawings depict only a typical embodiment of the invention and are not therefore to be considered to be limiting of its scope, the invention will be described and explained with additional specificity and detail through the use of the accompanying drawings as listed hereinbelow.

DETAILED DESCRIPTION OF THE PREFERRED EMBODIMENTS

Figure 1A:
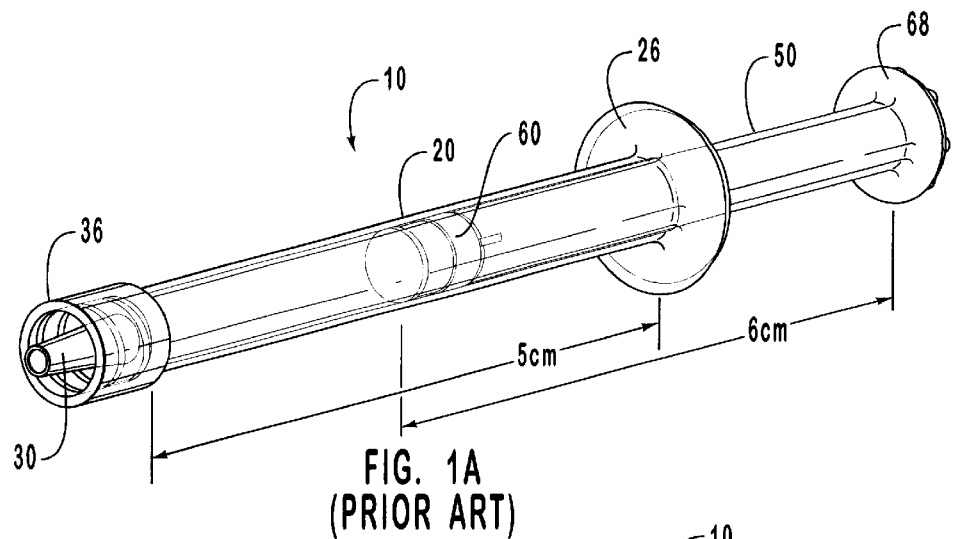
FIG. 1A is a perspective view of a prior art syringe 10.
Figure 1B:
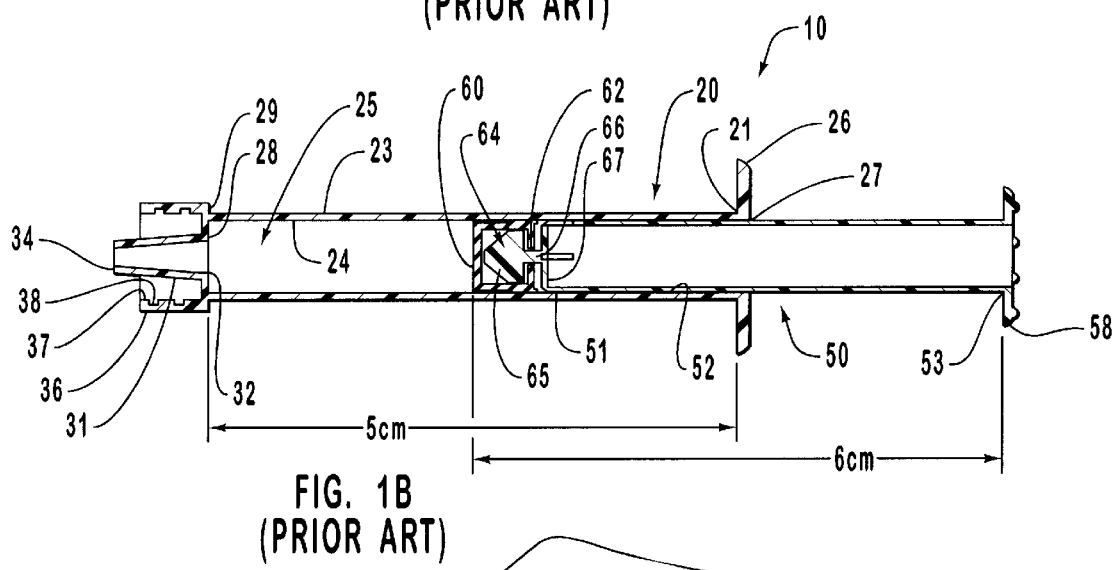
FIG. 1B is a cross-sectional view of the syringe 10 shown in FIG. 1A.

The present invention is directed to methods and apparatus for dispensing compositions, particularly dental compositions such as dental cements, restorative compositions and root canal sealers. More particularly, the present invention is directed to methods and apparatus for dispensing compositions in a controlled manner and with minimal effort. The present invention is especially useful in delivering two component compositions.

FIGS. 7A–7D illustrate a syringe 200 which is useful for dispensing compositions in accordance with the present invention. Syringe 200 is shown having a barrel 220 with a plunger 250 slidably engaged therein. Note that in contrast to syringe 10 shown in FIGS. 1A–1D, barrel 220 is much shorter than barrel 20. More particularly, barrel 220 is shown having a length which is almost half that of barrel 20. Accordingly, plunger 250 is much longer than barrel 220. Although the advantages of this configuration are fully related below it should be understood that the primary advantage resulting from this configuration is that a user can grasp the syringe and express all of the composition contained in the syringe without having to change the grasping position.

As also discussed in greater detail hereinbelow, barrel 220 is adapted for unidosing so that the syringe may be discarded after dispensing its contents in a single use. Other features will be appreciated after understanding the details of the elements of syringe 200 as set forth hereinbelow.

Barrel 220 has a top grasping end 221 opposite a bottom end 229 with a substantially cylindrical sidewall 222 extending therebetween. Sidewall 222 has an exterior surface 223 and an interior surface 224. Interior surface 224 defines a substantially cylindrical chamber 225 for holding a composition. Cylindrical chamber 225 is discussed in greater detail hereinbelow in reference to plunger 250.

Figure 8A:
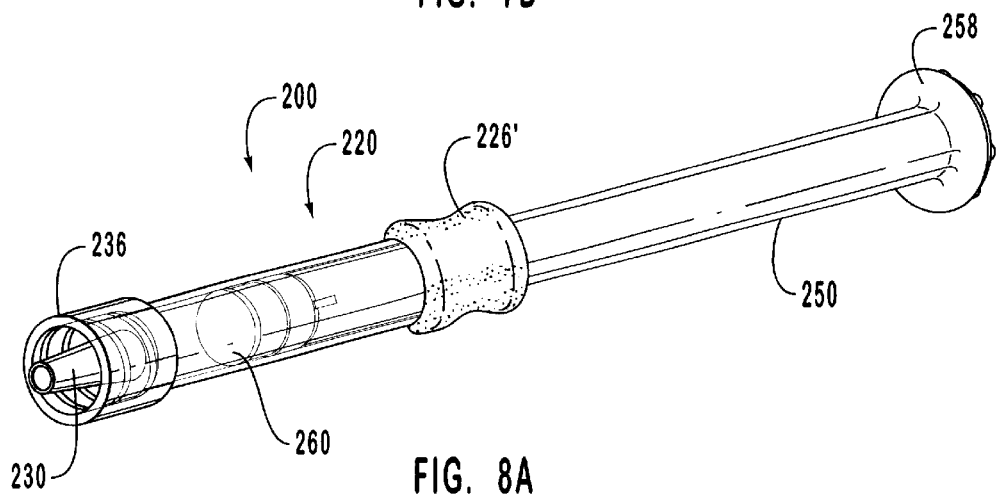
FIG. 8A is a side view of another embodiment of the inventive syringe.
Figure 8B:
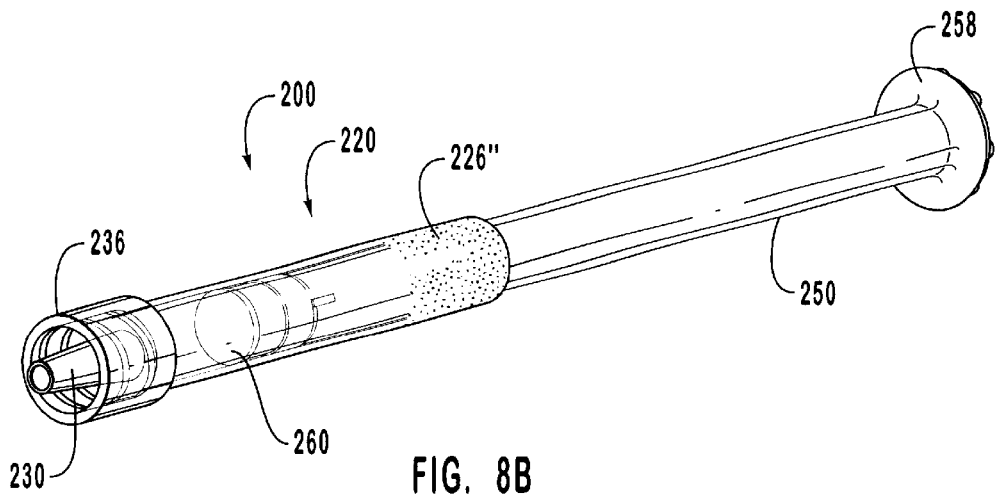
FIG. 8B is a side view of an additional embodiment of the inventive syringe.

Barrel 220 has a grasping handle 226 which is an annular flange extending radially and perpendicularly outward from sidewall 222 at top grasping end 221 of barrel 220. Grasping handle 226 is centrally located around opening 227 which has the same diameter as the interior surface 224 of chamber 225. Grasping handle 226 is an example of means for grasping the barrel such that a user s fingers can grasp the barrel. Additional examples of means for grasping the barrel include a raised engagement surface on the barrel as shown in FIG. 8A at 226', a textured engagement surface on the barrel as shown in a FIG. 8B at 226" or combinations of such surfaces. The engagement surface may be textured as shown by any suitable mechanism. Additionally, the engagement surface may be a smooth or textured groove around the perimeter of the barrel. As shown, the grasping handle 226 and the alternative grasping surfaces 226' and 226" are located at top grasping end 221 of barrel 220. While the grasping handle or grasping surface may also be located elsewhere on the barrel such as at bottom end 229, the location at top grasping end 221 is advantageous for several reasons. First, this enables a user to comfortably grasp the handle or surface of the barrel and the plunger. Additionally, it provides optimal visibility to the delivery site such that the user's view is not blocked by the user's fingers.

A radial extension 228 extends integrally from sidewall 222 at bottom end 229 inward to define an exit port 232. Exit port 232 is the opening which enables the composition in chamber 225 to exit. Radial extension 228 acts as a stop for plunger 250 as plunger 250 is depressed.

Exit port 232 is also the opening into channel 233 which enables channel 233 to communicate with chamber 225. Note that channel 233 is the interior surface of tapered exit tube 230. Channel 233 extends through tapered exit tube 230 and terminates at outlet 234.

Surrounding exit tube 230 is an attachment sleeve 236. Attachment sleeve 236 has an interior surface 237 with engagement threads 238 positioned thereon. A nozzle or tip 240, shown in FIGS. 7C and 7D, may be selectively attached to barrel 220 by coupling with threads 238. A variety of tips are available which may be attached such that channel 233 of exit tube 230 is in fluid communication with the tip for guided delivery of the composition to a desired location.

Figure 5:
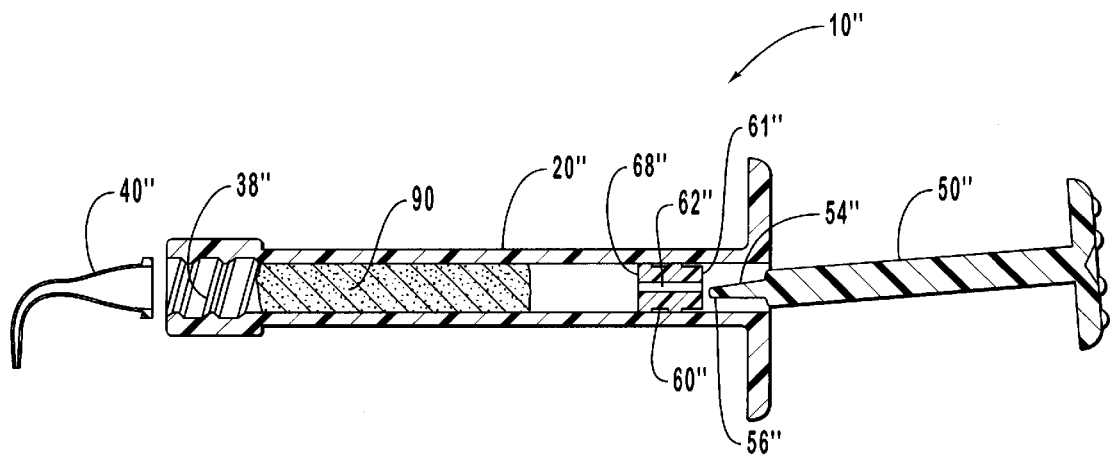
FIG. 5 is a perspective view of a prior art syringe 10" which is similar to syringe 10 shown in FIGS. 1A–1D except that syringe 10" has a sealing gasket 60" with a vent hole 62" for venting air. Also the tip is received into barrel 20" without an exit tube.

Note that exit tube 230 and attachment sleeve 236 are integral parts of barrel 220. Exit tube 230 and attachment sleeve 236 may also be replaced with a configuration as shown in FIG. 5. Barrel 20" has threads 38" which engage tip 40" and which are located within the barrel such that the chamber is essentially the interior part of the barrel above threads 38" or above tip 40" once positioned within barrel 20". Barrels within the scope of this invention may have this configuration or any other suitable configuration.

Tip 240 is configured to selectively attach in fluid communication with exit tube 230. To accomplish this end, tip 240 has a threaded end 242 for engagement with threads 238 of attachment sleeve 236. Opposite threaded end 242 is a flexible and angled spout 244 for guiding delivery of the composition to a desired location. It is of course envisioned that different sizes and shapes of spouts 244 can be used depending on the type and intended use of the composition. Furthermore, in alternative embodiments, tip 240 may be permanently attached to bottom end 229 or means other than threads may be used to attach different sizes and/or shapes of tips. Additionally, syringes within the scope of the present invention need not necessarily utilize a separate tip or have an integral tip.

Plunger 250 has a distal lead end 251 opposite from a proximal pushing end 253 with a stem 252 extending therebetween. Plunger 250 is sized to be slidably received within chamber 225 through opening 227 at top grasping end 221. Plunger 250 has a length that permits it to be advanced to bottom end 229 while a significant portion of plunger 250 remains extending beyond opening 227. The length of plunger 250 is discussed in greater detail hereinbelow.

Radially extending outward at pushing end 253 of plunger 250 is an annular pushing handle 258 used in advancing plunger 250. Note that the pushing handle of the plunger is preferably configured as shown at 258 which is described in greater detail in U.S. Design Pat. No. 322,317. U.S. Design Pat. No. 322,317, which issued to Dan E. Fischer on Dec. 10, 1991 and is owned by Ultradent Products, Inc., is hereby incorporated by reference.

Figure 7A:
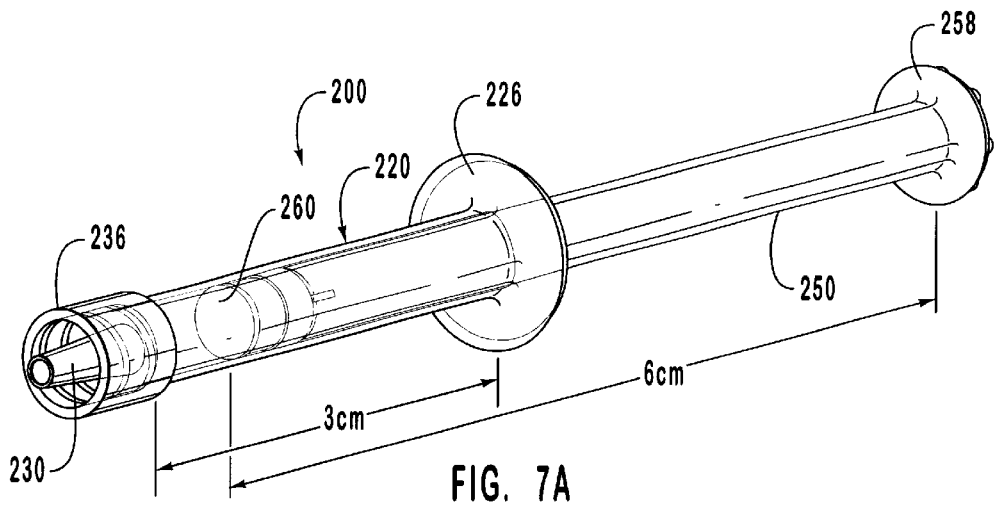
FIG. 7A is a perspective view of an embodiment of the inventive syringe.
Figure 7B:
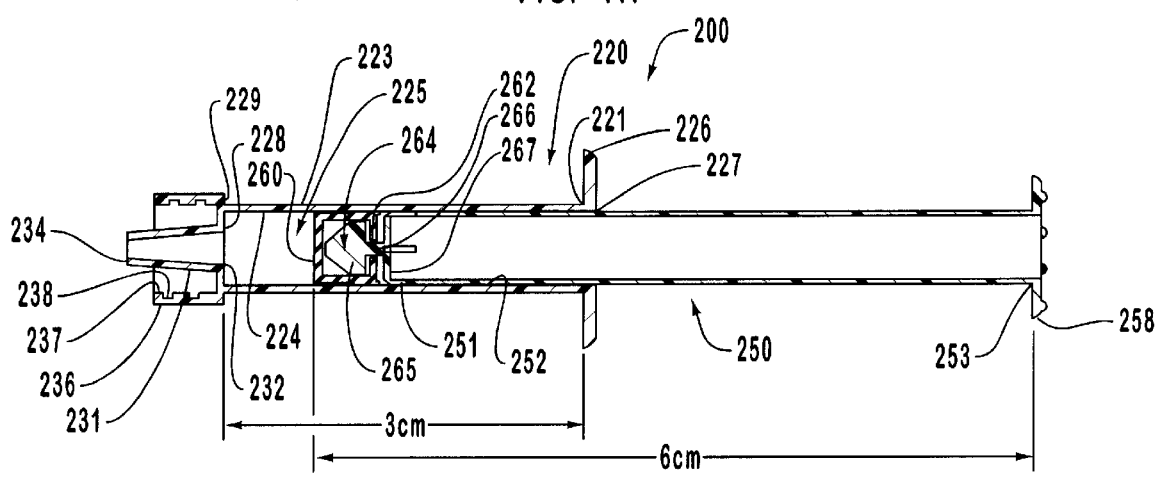
FIG. 7B is a cross-sectional view of the syringe shown in FIG. 7A.

Positioned at lead end 251 of plunger 250 is a cylindrically shaped sealing gasket 260. More particularly, gasket 260 is coupled to stem 252 via a gasket holder as shown in FIG. 7B at 264. Gasket 260 is made of a soft, compressible, sealing material, such as rubber, which allows the exterior surface of gasket 260 to seal against interior surface 224 of chamber 225 as plunger 250 is advanced within chamber 225 or selectively slid down to bottom end 229. Gasket holder 264 has a post 266 with a head element 265 integrally extending at one end and a base 267 integrally extending from the other end. Head element 265 and post 266 are inserted into an opening 262 of gasket 260 which expands such that head element 265 can be inserted therein and then elastically return to its original size such that head element 265 is removably held in gasket 260. Base 267 is connected to stem 252 to hold gasket holder 264 in position.

A plunger within the scope of the present invention includes at least a stem and preferably also includes a handle such as pushing handle 258. The plunger may also include a gasket held by a gasket holder extending from a stem as discussed above. The plunger may also be shaped like the plunger shown and described in U.S. Pat. No. 4,986,820, which is hereby incorporated by reference. U.S. Pat. No. 4,986,820, which is entitled "Syringe Apparatus Having Improved Plunger", issued to Dan E. Fischer and is owned by Ultradent Products, Inc. Note that the entire plunger disclosed in U.S. Pat. No. 4,986,820 is integral. As described hereinbelow, specialized plungers may also be utilized which deploy a paddle. Examples of such specialized plungers are disclosed in U.S. patent application Ser. No. 09/356,009 which is hereby incorporated by reference. Ser. No. 09/356,009 which is also owned by Ultradent Products, Inc. is entitled "Integrated Mixing and Dispensing Apparatus"and was filed on Jul. 16, 1999 for Dan E. Fischer and Bruce McLean. In any event, as discussed below, plungers within the scope of the present invention are configured to be significantly longer than the length of the chamber of the barrel. The plungers disclosed herein are examples of plunger means for advancing the composition positioned within the barrel through the exit port at the first end of the barrel.

Figure 7C:
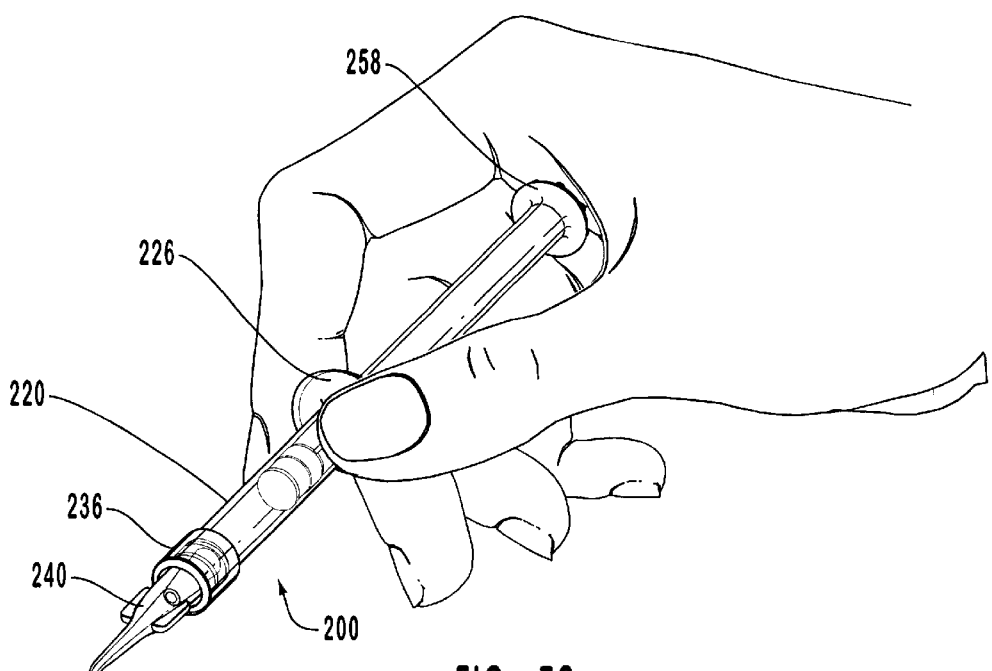
FIG. 7C is a perspective view of the syringe shown in FIG. 7A loaded with a composition and with the plunger positioned to initially express the composition from the syringe.
Figure 7D:
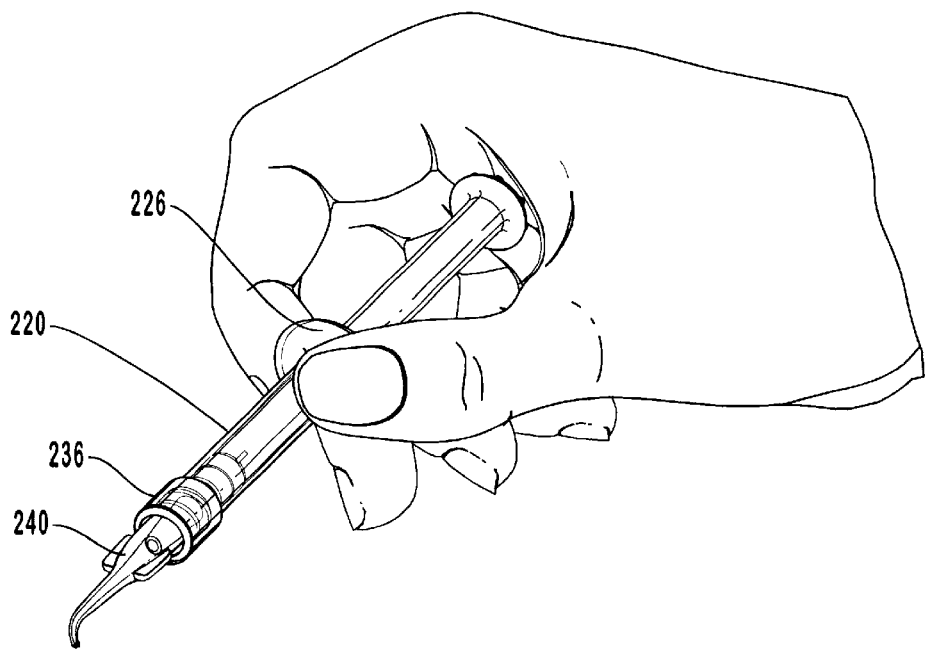
FIG. 7D is a perspective view of the syringe shown in FIG. 7A after the plunger has been fully depressed to express all of the composition from the syringe.

Plunger 250 is shown having a length which is about twice as long as chamber 225. This is perhaps most clearly seen in FIG. 7D, wherein plunger 250 is fully advanced within chamber 225, since the portion of plunger 250 extending out of chamber 225 has a length that is at least equal to that of the portion of plunger 250 within chamber 225. This length provides a significant advantage over prior art syringes. For example, reference to syringe 10 as depicted in FIGS. 1C and 1D shows that a user must change hand positions as the plunger is depressed while reference to FIGS. 7C and 7D shows that the plunger can be fully depressed while holding syringe 200 in a single position.

To appreciate the importance of not altering the position in which the syringe is held, it is necessary to understand the manner in which such syringes are typically held and used. The grip shown being utilized in FIGS. 1C and 7C wherein the proximal pushing end of the plunger is pressed against the palm of the user's hand while the user's fingertips pull the grasping handle of the barrel to advance the plunger within the chamber is particularly useful in dentistry. This grip enables the user to deliver the composition contained in the chamber with a high degree of control. FIG. 1C shows the fingertips of the index finger and thumb positioned on grasping handle 26 while FIG. 7C shows a more secure grip. More particularly, FIG. 7C shows the fingertips of the middle finger, the index finger and the thumb holding grasping handle 226. Either grip may be utilized although, as mentioned, the grip shown in FIG. 7C is more secure and it also enables the user to apply greater pressure. In any event, these grips are useful in dentistry as they enable a user to hold the syringe in such a manner the user may maneuver the syringe as desired within a patient's mouth while maintaining a high degree of control.

Figure 1C:
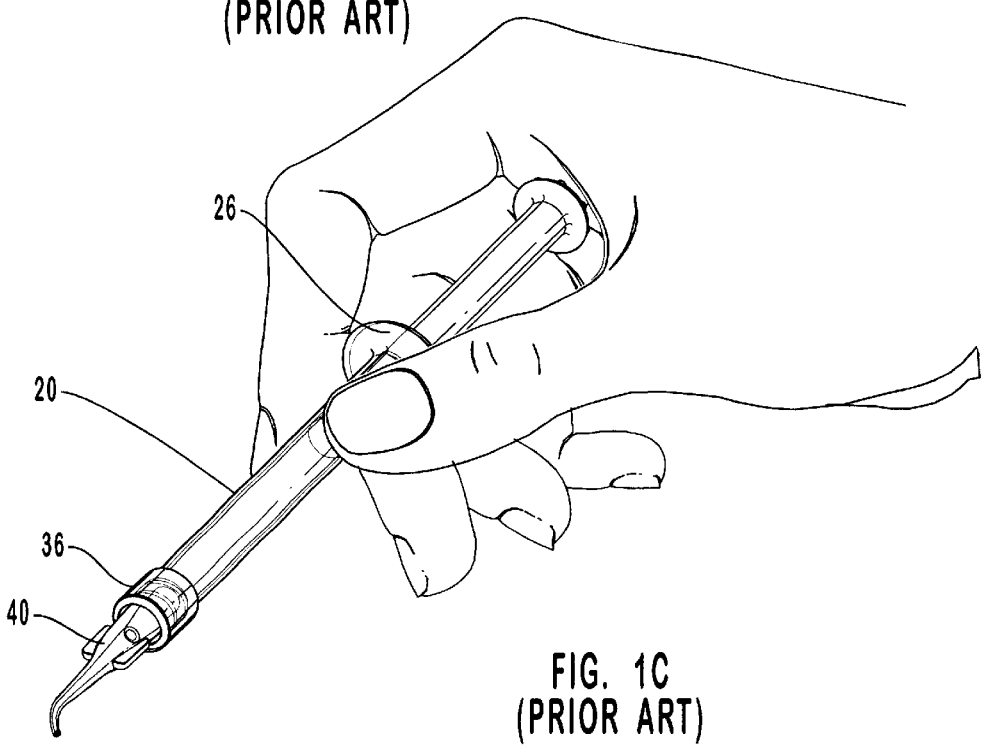
FIG. 1C is a perspective view of the syringe 10 shown in FIG. 1A loaded with a composition and with the plunger positioned to initially express the composition from the syringe.
Figure 1D:
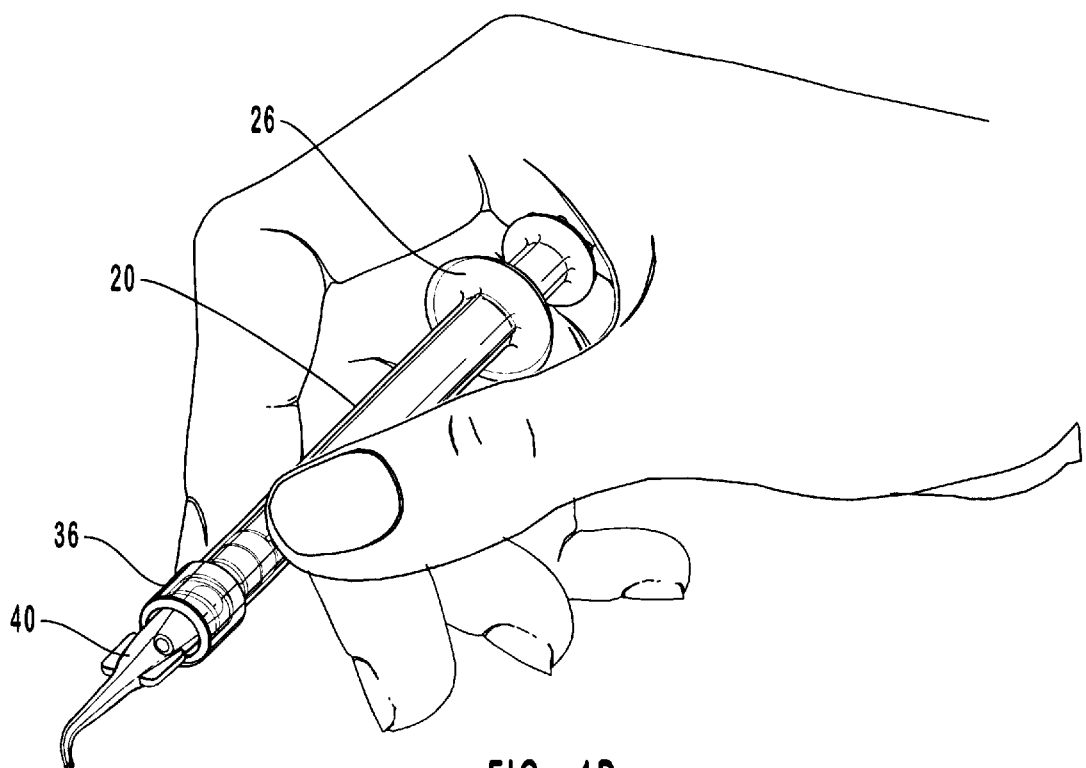
FIG. 1D is a perspective view of the syringe 10 shown in FIG. 1A after the plunger has been fully depressed to express all of the composition from the syringe.
Figure 2:
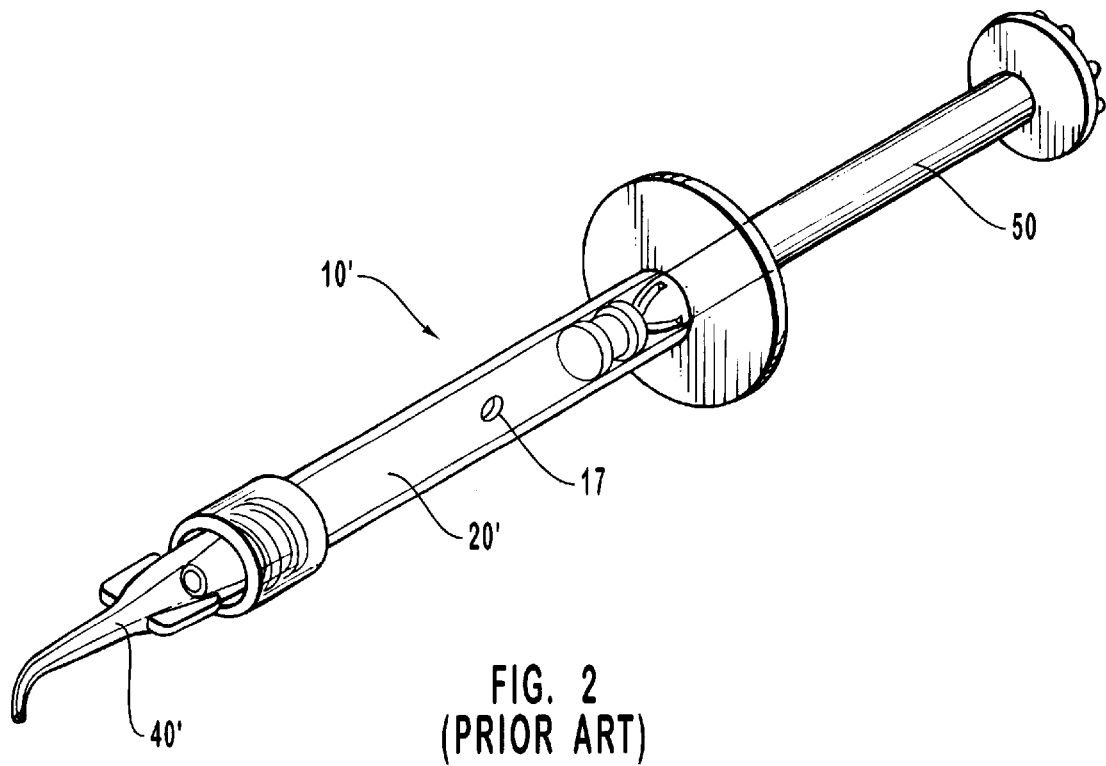
FIG. 2 is a perspective view of a prior art syringe 10' which is identical to syringe 10 shown in FIGS. 1A–1D except that syringe 10' has a barrel 20' with a vent hole 15 for venting air.

As mentioned above, it is necessary to change the grip used with a prior art syringe such as that shown in FIGS. 1C and 1D. As plunger 50 is pushed farther into chamber 25, the user experiences increasing difficulty in pushing the plunger. More particularly, when the fingers are extended they can more easily push downward, however, as they draw closer to the palm with this particular grip the fingers do not have adequate strength to press grasping handle 26 toward the user's palm or toward pushing end 53 of barrel 20. The difficulty experienced makes it necessary for a user to shift from the position shown in FIG. 1C to that shown in FIG. 1D. This change in position may result in undesired movement of the syringe. As the grasp of the user is altered, the syringe may be inadvertently swung to the side away from the intended delivery site. The movement may be slight, however, some substances which may safely contact enamel or dentin can be potentially harmful to soft tissues such as the gums.

In addition to undesired movement of the syringe as well as the resulting interruption to a particular procedure, the configuration of syringe 10 increases the hand fatigue which a dental practioner experiences. More particularly, many users attempt to compress a plunger into a chamber until it is necessary to regrasp the syringe due to the resistant experienced. Instead of stopping while it is still easy to compress, users typically strains to deliver the composition until the point is reached when it becomes to difficult for that particular hand grasp. When frequently repeated, this exertion can cause hand fatigue.

The length of plunger 250 relative to that of chamber 220 enables the syringe to be grasped in one position and then to be used to continuously deliver the composition in chamber 220 as shown in FIGS. 7C and 7D. As indicated above, this is a significant advantage as it eliminates the possibility of accidentally moving the syringe due to altering one's grasp of the syringe. Not only is it unnecessary to regrasp the syringe during the depression of plunger 250 into chamber 220, the configuration of syringe 200 also enables a user to exert less effort in delivering the composition. Further, the configuration enables a user to exert essentially the same amount effort throughout the depression of the plunger within the chamber of the barrel.

As indicated in the section above entitled Background of the Invention, chamber 25 is designed to hold about 1.2 ml and the length of the chamber is about 5 cm while the length of the plunger is about 6 cm. The ratio of the length of plunger 50 to the length of the chamber 25 is accordingly, as also noted above, 1.2:1.

Plunger 250 is shown having a length which is about twice as long as chamber 225, as indicated above, so that the ratio of the length of the plunger to the length of the chamber is about 2:1. More particularly, when the chamber is designed to hold a composition ranging from about 0.2 ml to about 0.6 ml, then the length of the chamber is about 3 cm and length of the plunger is about 6 cm. The syringe shown at 200 depicts such a configuration. The length of the chamber is most preferably 3.15 cm when the barrel is used with a plunger having a length of about 6.2 cm; this yields a ratio of 1.97:1. While the preferred ratio is about 2:1, the ratio of the length of the plunger to the length of the chamber may also be no less than about 1.8:1 and still enable a user to deliver the entire content of the composition held in the chamber without regrasping the syringe. The ratio may even be as low as no less than about 1.5:1.

Chamber 225 can have any size and shape as long as the length of the chamber is significantly less than that of the length of the plunger, as discussed above. However, chamber 225 is preferably sized to hold small quantities of a composition. For example, as indicated above, chamber 225 of barrel 220 is preferably configured to hold an amount of a composition ranging from about 0.2 ml to about 0.6 ml. Chamber 225 is more preferably configured to hold an amount of a composition ranging from about 0.25 ml to about 0.3 ml. By utilizing a barrel having a chamber sized to hold such preferred volumes, the chamber and the plunger may have the optimal length ratios discussed above, which enable a user to easily deliver metered amounts as needed.

The preferred barrel volume corresponds with the amount needed of most dental compositions for a single use when utilized in particular procedures. While many compositions can be held in a syringe and used at various times, many dental compositions which are formed by mixing two parts cannot be used after a certain period of time has expired as the compositions may set or harden. In such instances, it is particularly desirable that the chamber hold no more than is necessary for the single use as any more will be wasted. Accordingly, limiting chamber 225 to holding small quantities of a composition, enables syringe 200 to be used for a single application without leaving any excess composition to be wasted. Since loading a syringe for unidosing requires less composition, the result is a less expensive procedure. Such unidoses are also sized appropriately for laboratory uses in dental schools as the dental students typically need only very small quantities.

Figure 3:
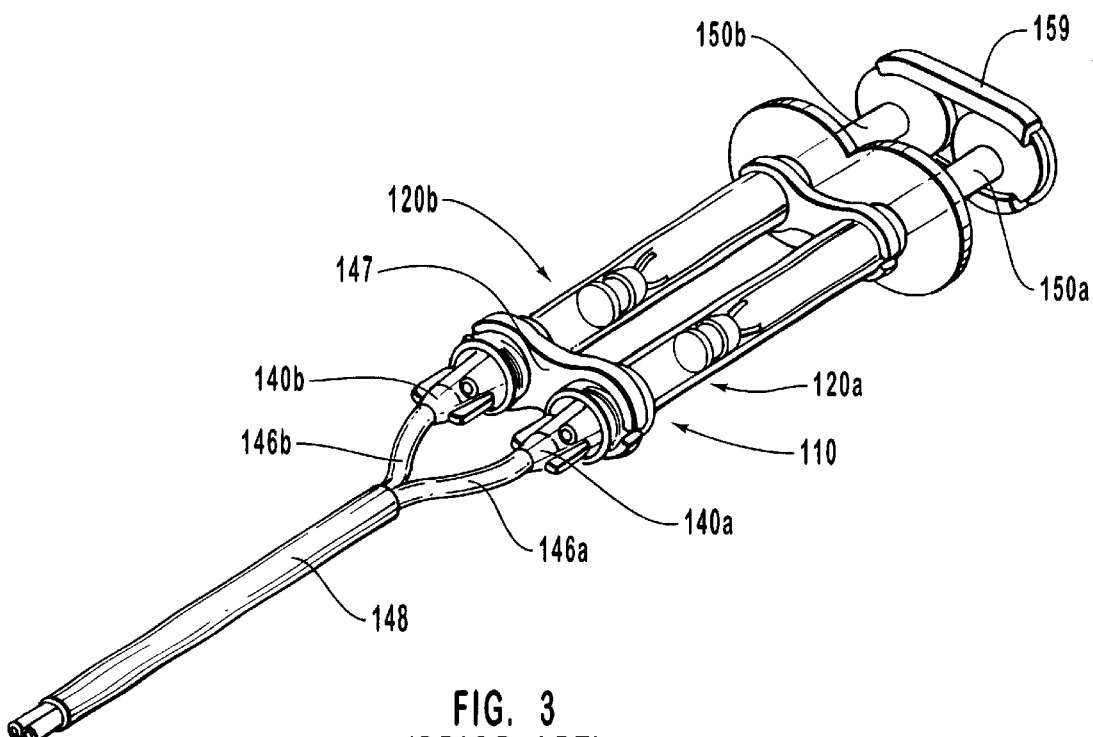
FIG. 3 is a perspective view of a two-syringe device used to deliver two component compositions into the barrels of syringes for delivery onto a substrate such as a dental preparation.
Figure 6:
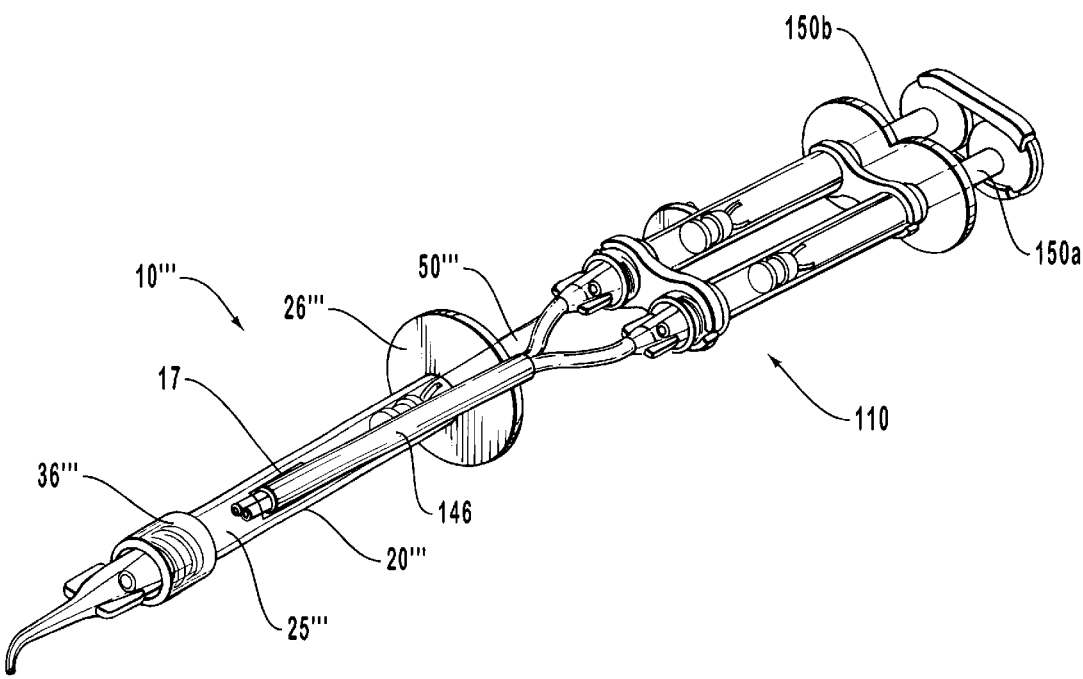
FIG. 6 is a perspective view of a prior art syringe 10'" which is identical to syringe 10 shown in FIGS. 1A–1D except that syringe 10'" has a barrel 20'" with an access port 17 for venting air. Note that a modified version of the two-syringe device depicted in FIG. 3 is shown being used in FIG. 6 to deliver the two components into barrel 20'".
Figure 9:
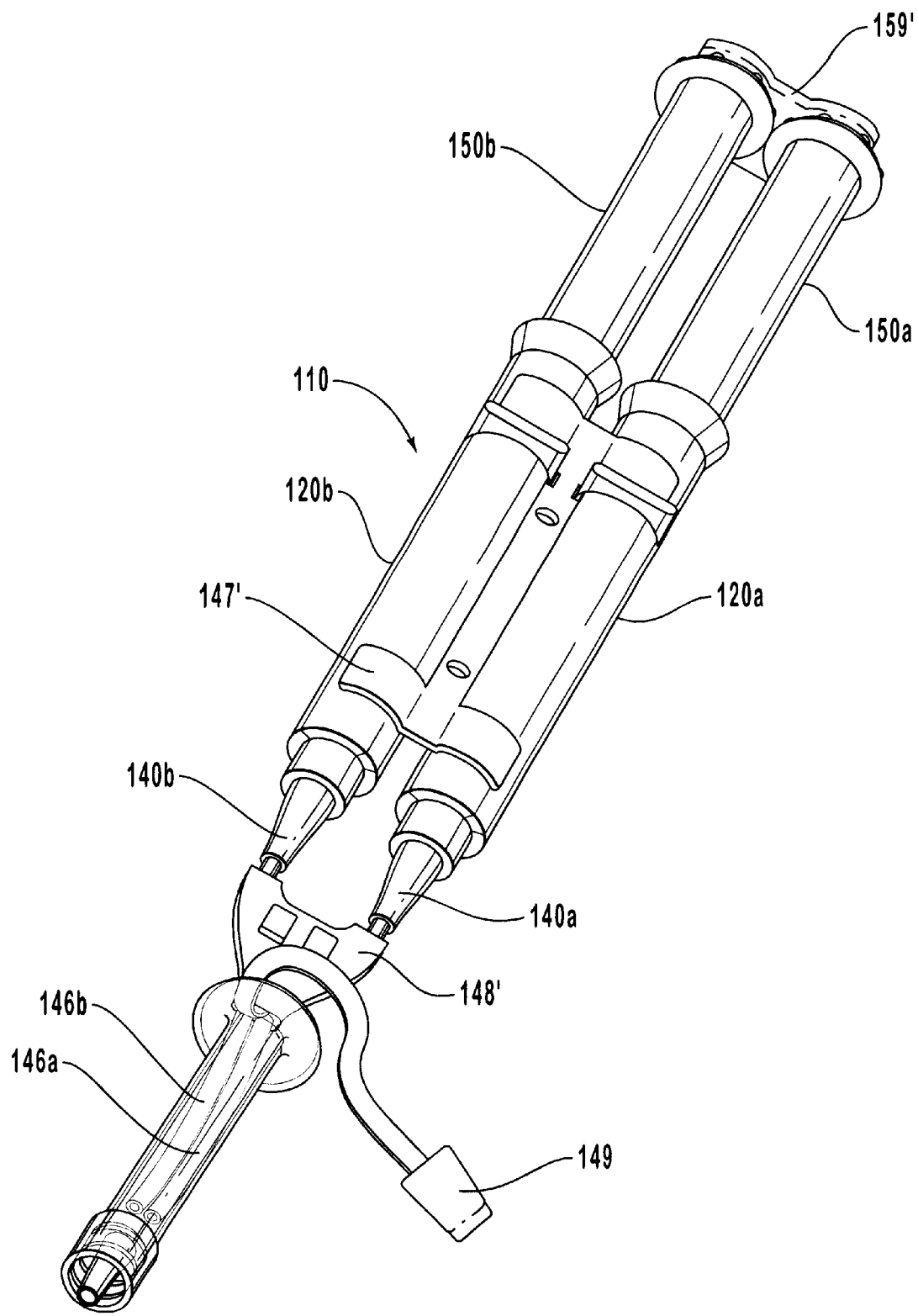
FIG. 9 is a perspective view of a two-syringe device for use in introducing two components of a two-part composition into the syringe in FIGS. 7A–7D for subsequent mixing therein.

FIG. 9 depicts a two-syringe device 110' which is very similar to that shown in FIGS. 3 and 6 being utilized to deliver the two part composition into chamber 225. Two-syringe device 110' differs from two-syringe device 110 in several respects and is more similarly configured to the two-syringe device disclosed in U.S. Pat. No. 5,290,259. Note that tubing members 146a' and 146b' of two-syringe device 110' are curved. Curved tubing members 146a' and 146b' are also held together with a flared collar 148' at the upper end of the curved tubing members instead of a collar such as collar 148 which is tubular and is attached along the length of the tubing members toward their terminal ends. Collar 148' also has a cap 149 tethered for covering the terminal ends of the tubular members. Barrel clamp 147' and plunger clamp 159' are also configured differently from their respective counterparts in two-syringe device 110', barrel clamp 147 and plunger clamp 159.

The curvature of curved tubing members 146a' and 146b' enables them to easily reach bottom end 229 of barrel 220 as shown; more particularly the radial extension which extends integrally from sidewall 222 at bottom end 229. The length of chamber, however, is the most important factor in enabling compositions to be delivered to the bottom end 229 of barrel 220. Due to the relatively short length of chamber 225 and the resultant ability to easily reach the bottom of the barrel, air is not entrained during delivery or at least air entrainment is minimized. Since no air bubbles are trapped within the composition or the amount of entrapped air is very small, it is not necessary to vent air out as plunger 250 is depressed into chamber 225. More specifically, it is not necessary to vent air from chamber 225 through an air vent in the barrel or in the plunger. The minimization of air entrapment makes syringe 200 very useful in delivering two part or A/B compositions.

The composition is first delivered to bottom end 229 of chamber 225 to avoid trapping air bubbles within chamber 225. Then as the composition is delivered curved tubing members 146a' and 146b' of two-syringe device 110' are slowly removed until chamber 225 is filled with the two parts of the composition as desired. Note that two part compositions may be delivered by other suitable devices such as two-syringe device 110. Also note that while reference is made to two-component systems or A and B component systems, it should be understood that the methods and apparatus of the present invention will accommodate systems having more than two components. Additionally, the diameters of syringe barrels 150a' and 150b' may be altered as necessary to effect differing ratios of the A and B components. For example, if A and B components are to be added in substantially equal amounts, both syringe barrels 150a' and 150b' are substantially identical as shown. If, however, it were desired to add two parts of A to one part of B, syringe barrel 150a would have a cross-sectional area twice that of syringe barrel 150b. It will be appreciated that other modifications may be made in the respective sizes of syringe barrels 150a and 150b to accommodate other mixing ratios. Markings on the sides of syringe barrels 150a and 150b can be used to measure a desired volume to be introduced into syringe barrel 220, or one may look at markings optionally provided on syringe barrel 220.

Figure 4:
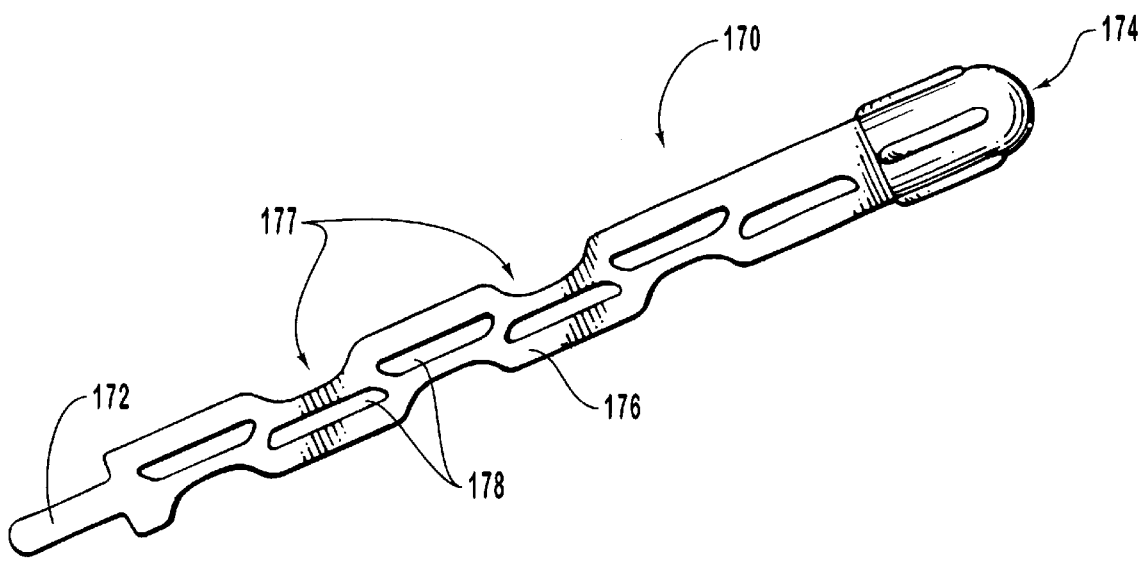
FIG. 4 is a perspective view of a mixer element or spatulas used for mixing two component compositions.
Figure 10:
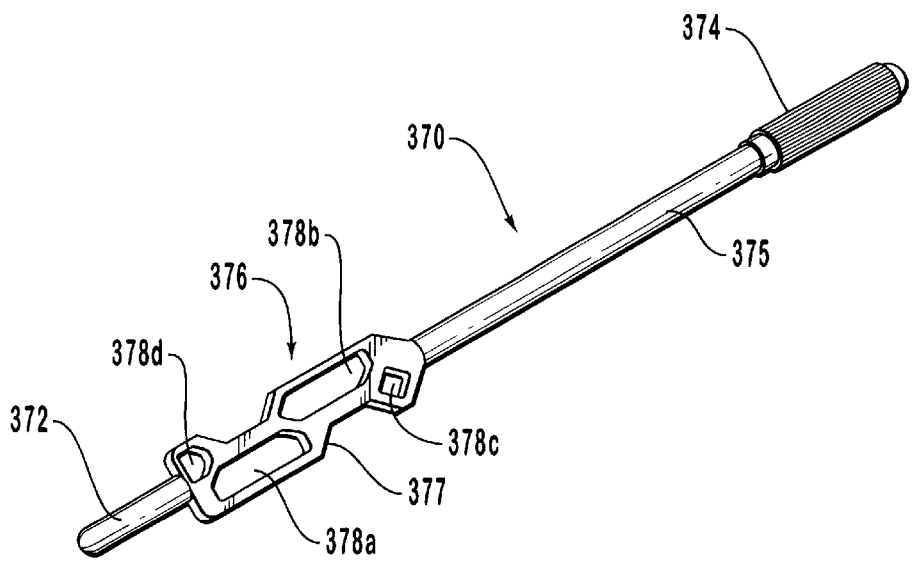
FIG. 10 is a perspective view of a mixer element or paddle member used for mixing the two-part composition within the syringe of FIGS. 7A–7D.
Figure 11:
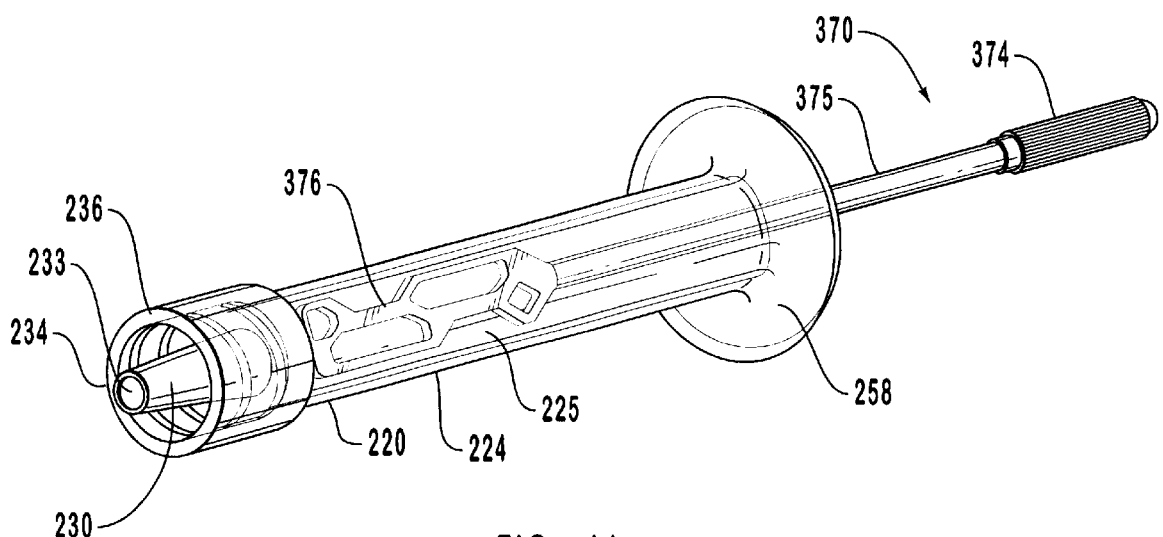
FIG. 11 is a perspective view of the mixer element or paddle member in FIG. 10 inserted within the syringe.

After delivering the parts or components of the composition into chamber 225, they are then ready to be mixed. As previously indicated, it has been determined that the most effective mixing of the A and B components utilizing the apparatus of the present invention is accomplished by loading the two components side-by-side within chamber 225 rather than one on top of the other. A mixer element such as those disclosed in U.S. Pat. No. 5,328,462 as referenced above in relation to FIG. 4 may be utilized. FIG. 10 provides a perspective view of another mixer element at 370 which may also be used for mixing a two-part composition within chamber 225 of syringe 200. Mixer element 370 is shown in FIG. 11 inserted into barrel 220 and ready for rotation until the two components are thoroughly mixed together. The mixer elements disclosed herein are examples of mixer element means for mixing at least two components of a composition within a chamber of a barrel.

As shown in FIGS. 10 and 11, mixer element 370 has a rotation handle 374 which functions similarly to handle or finger grip member 174. Mixer element 370 has an insertion or rotation pin 372 positioned at the opposing end from rotation handle 374 which is configured similarly to that shown at 172. Dunng use, as shown in FIG. 11, mixer element 370 is slid within chamber 225 through opening 227 such that rotation pin 372 is inserted within channel 373 and then allowed to rotate within channel 233. Mixer element 370 has a length slightly longer than chamber 225 so that rotation handle 374 projects out of top grasping end 221 when rotation pin 372 is inserted within channel 233. Once mixer element 370 is properly positioned, rotation of handle 374 causes mixer element 370 to rotate within chamber 225, thereby mixing the components into a homogeneous composition.

The width of mixer element 370 is preferably about the same as the internal diameter of chamber 225. This sizing enables more complete mixing by scraping material from interior surface 224 of chamber 225. As illustrated in FIGS. 10 and 11, it is presently preferred that mixer element 370 have a stem 375 with a paddle portion 376 above rotation pin 372. Paddle portion 376 may have any suitable length. For example, it may correspond with the length of chamber 225 or be somewhat shorter than chamber 225. Paddle portion 376 may have a plurality of variously sized and shaped cutouts identified at 378a–d. Any shape may be utilized, however, the cutouts are shown as polygonals. More particularly, cutout 378a is a generally "D" shaped hexagon while 378b is also a hexagon with a different configuration. Cutout 378c and 378d have a relatively smaller size and are respectively a square and a pentagon. The cutouts function as means for effecting turbulence within chamber 24 in order to obtain more rapid and complete mixing. Note that paddle portion 376 also has recessed portions 377 which are essentially cutouts from the sides thereof. Recessed portions 377 enable paddle portion 376 to more easily rotate within chamber 225. Recessed portions 377 also augment the generation of turbulence created by cutouts 378 as paddle 370 is rotated. Such mixing can be accomplished with little or no entrainment of air bubbles. Once the composition is mixed within barrel 220, plunger 250 is positioned within chamber 225 at top grasping end 221 in contact with the composition so that the composition may be pressed through channel 233, out of outlet 234 and through tip 240 so as to be delivered through spout 244 and onto the desired delivery site.

It will be appreciated that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Letters Patent is:

1. A method for dispensing a composition from a syringe so that the syringe is grasped in a single position, the method comprising the steps of:

obtaining a syringe including
a hollow elongated barrel having a sidewall extending between a top grasping end and an opposing bottom end, the sidewall having an interior surface defining a chamber, the barrel further having means for grasping the barrel located at the proximal grasping end of the barrel,
a composition held within the chamber, and
plunger means for advancing the composition positioned within the chamber out of the barrel, the plunger means having a distal lead end opposite from a proximal pushing end, and wherein the length of the plunger means relative to the length of the chamber yields a ration which is no less than about 1.5:1;

grasping the syringe with the proximal pushing end of the plunger means against the palm of the user's hand and with the user's fingertips against the grasping means; and continuously delivering the composition from the chamber by advancing the plunger means within the chamber until the distal lead end of the plunger means contacts the bottom end of the chamber through pulling the grasping means while pushing the proximal pushing end against the user's palm, without regrasping the syringe such that the syringe is not moved relative to a delivery site during the delivery of the composition to the delivery site due to movement of the user's hand.

2. A method as recited in claim 1, wherein the chamber is sized such that it can hold only sufficient composition for use in a single dental restorative procedure.

3. A method as recited in claim 1, wherein the barrel and the plunger means are configured for ventless delivery of the composition out of the chamber.

4. A method for dispensing a composition from a syringe so that the syringe is grasped in a single position, the method comprising the steps of:

obtaining a syringe including
   a hollow elongated barrel having a sidewall extending between a top grasping end and an opposing bottom end, the sidewall having an interior surface defining a chamber, the barrel her having means for grasping the barrel located at the proximal grasping end of the barrel,
   a composition held within the chamber, and
   plunger means for advancing the composition positioned within the chamber out of the barrel, the plunger means having a distal lead end opposite from a proximal pushing end, the plunger means having a length that is at least twice that of the chamber of the barrel such that when the plunger means is fully advanced within the chamber a portion of the plunger extends out of the chamber with a length that is at least equal to that of the chamber;
grasping the syringe with the proximal pushing end of the plunger means against the palm of the user's hand and with the user's fingertips against the grasping means; and
continuously delivering the composition from the chamber by advancing the plunger means within the chamber until the distal lead end of the plunger means contacts the bottom end of the chamber through pulling the grasping means while pushing the proximal pushing end against the user's palm, without regrasping the syringe such that the syringe is not moved relative to a delivery site during the delivery of the composition to the delivery site due to movement of the user's hand.

5. A method as recited in claim 4, wherein the chamber is sized such that it can hold only sufficient composition for use in a single dental restorative procedure.

6. A method as recited in claim 4, wherein the barrel and the plunger means are configured for ventless delivery of the composition out of the chamber.

7. A method for dispensing a dental composition of two or more components from a syringe so that the syringe is grasped in a single position, the method comprising the steps of:

obtaining a hollow elongated barrel having a sidewall extending between a top grasping end and an opposing bottom end, the sidewall having an interior surface defining a chamber for holding a composition, the barrel further having means for grasping the barrel located at the proximal grasping end of the barrel,
delivering a dental composition having at least two components into the chamber via an opening at the top grasping end of the barrel,
mixing the components of the dental composition in the chamber, obtaining plunger means for advancing the composition positioned within the barrel through the exit port at the first end of the barrel, wherein the plunger means has a distal lead end opposite from a proximal pushing end, and wherein the length of the plunger means relative to the length of the chamber yields a ratio which is no less than about 1.5:1,
inserting the distal lead end of the plunger means into the chamber to provide a syringe,
grasping the syringe with the proximal pushing end of the plunger means against the palm of the user's hand and with the user's fingertips against the grasping means,
continuously delivering the dental composition from the chamber by advancing the plunger means within the chamber until the distal lead end of the plunger means contacts the bottom end of the chamber through pulling the grasping means while pushing the proximal pushing end against the user's palm, without regrasping the syringe.

8. A method as recited in claim 7, wherein the chamber is sized such that it can hold only sufficient dental composition for use in a single dental restorative procedure.

9. A method as recited in claim 7, wherein the delivering step includes initially depositing the components of the dental composition in the chamber toward the bottom end of the barrel and then continuing to deposit the components in the chamber.

10. A method as recited in claim 7, wherein the delivering step includes depositing the components of the dental composition within the chamber in a manner such that the components are side by side along the longitudinal axis of the chamber.

11. A method as recited in claim 7, wherein the delivering step includes:
expressing the components of the dental composition from a two-syringe device positioned to initially deposit the components in the chamber toward the bottom end of the barrel and
moving the two-syringe device away from the bottom end of the barrel while continuing to express the components until appropriate amounts of the components are deposited such the dental composition is delivered substantially free of entrained air.

12. A method as recited in claim 7, wherein the barrel and the plunger means are configured for ventless delivery of the composition out of the chamber.

13. A method as recited in claim 7, wherein the mixing step includes inserting and then rotating a mixer element means for mixing the components of the dental composition within the chamber of the barrel.

14. A method as recited in claim 7, wherein the mixing step includes
inserting a mixer element into the chamber through the opening at the top end of the barrel;
rotating the mixer element to mix the components so as to form a mixed dental composition; and
removing the mixer element from the chamber.

15. A method as recited in claim 7, wherein the mixing step is achieved with a mixer element comprising a stem having a handle at one end and a paddle portion above a rotation pin at the other end.

16. A method for dispensing a dental composition of two or more components from a syringe so that the syringe is grasped in a single position, the method comprising the steps of:
obtaining a hollow elongated barrel having a sidewall extending between a top grasping end and an opposing bottom end, the sidewall having an interior surface defining a chamber for holding a composition, the barrel further having means for grasping the barrel located at the proximal grasping end of the barrel, delivering a dental composition having at least two components into the chamber via an opening at the top grasping end of the barrel, mixing the components of the dental composition in the chamber, obtaining plunger means for advancing the composition positioned within the barrel through the exit port at the first end of the barrel, wherein the plunger means has a distal lead end opposite from a proximal pushing end, the plunger means having a length that is at least twice that of the chamber of the barrel, inserting the distal lead end of the plunger means into the chamber to provide a syringe, grasping the syringe with the proximal pushing end of the plunger means against the palm of the user's hand and with the users fingertips against the grasping means, continuously delivering the dental composition from the chamber by advancing the plunger means within the chamber until the distal lead end of the plunger means contacts the bottom end of the chamber through pulling the grasping means while pushing the proximal pushing end against the user's palm, without regrasping the syringe such that the syringe is not moved relative to a delivery site during the delivery of the dental composition to the delivery site due to movement of the user's hand.

17. A method as recited in claim 16, wherein the chamber is sized such that it can hold only sufficient dental composition for use in a single dental restorative procedure.

18. A method as recited in claim 16, wherein the delivering step includes initially depositing the components of the dental composition in the chamber toward the bottom end of the barrel and then continuing to deposit the components in the chamber.

19. A method as recited in claim 16, wherein the delivering step includes:
expressing the components of the dental composition from a two-syringe device positioned to initially deposit the components in the chamber toward the bottom end of the barrel and moving the two-syringe device away from the bottom end of the barrel while continuing to express the components until appropriate amounts of the components are deposited such the dental composition is delivered substantially free of entrained air.

20. A method as recited in claim 16, wherein the barrel and the plunger means are configured for ventless delivery of the composition out of the chamber.

21. A method as recited in claim 16, wherein the mixing step includes inserting and then rotating a mixer element means for mixing the components of the dental composition within the chamber of the barrel.

22. A method for dispensing a dental composition of two or more components from a syringe so that the syringe is grasped in a single position, the method comprising the steps of:

obtaining a hollow elongated barrel having a sidewall extending between a top grasping end and an opposing bottom end, the sidewall having an interior surface defining a chamber for holding a composition, the barrel further having a grasping handle located at the proximal grasping end of the barrel, delivering a dental composition having at least two components into the chamber via an opening at the top grasping end of the barrel, mixing the components of the dental composition in the chamber, obtaining a plunger, the plunger means having a distal lead end opposite from a proximal pushing end, the plunger having a length that is at least twice that of the chamber of the barrel, inserting the distal lead end of the plunger into the chamber to provide a syringe, grasping the syringe with the proximal pushing end of the plunger against the palm of the user's hand and with the user's fingertips against the grasping handle, continuously delivering the dental composition from the chamber by advancing the plunger within the chamber until the distal lead end of the plunger means contacts the bottom end of the chamber through pulling the grasping handle while pushing the proximal pushing end against the user's palm, without regrasping the syringe such that the syringe is not moved relative to a delivery site during the delivery of the dental composition to the delivery site due to movement of the user's hand.

23. A syringe for dispensing a composition, the syringe comprising:
(a) a hollow elongated barrel having:
a sidewall extending between a top grasping end and an opposing bottom end, the sidewall having an interior surface defining a chamber for holding a composition,
the barrel having an opening at the top grasping end for accessing the chamber and having an exit port at the bottom end for enabling the composition to exit the chamber, and
means for grasping the barrel, the grasping means being located at the proximal grasping end of the barrel; and
(b) plunger means for advancing the composition positioned within the barrel through the exit port at the bottom end of the barrel,
wherein the plunger means has a distal lead end opposite from a proximal pushing end,
wherein the plunger means has a length which when fully inserted into the barrel, extends sufficiently beyond the grasping means so as to enable a user to grasp the syringe in a single position with the proximal pushing end against the palm of the user's hand and the user's fingertips against the grasping means and to then continuously deliver a composition from the chamber by advancing the plunger means within the chamber until the distal lead end of the plunger means contacts the bottom end of the chamber through pulling the grasping means while pushing the proximal pushing end against the user's palm.

24. A syringe as recited in claim 23, wherein the means for grasping the barrel is a grasping handle.

25. A syringe as recited in claim 23, wherein the chamber is sized such that it can hold only sufficient composition for use in a single dental restorative procedure.

26. A syringe as recited in claim 23, wherein the chamber is sized such that it can hold only a volume ranging from about m about 0.2 ml to about 0.6 ml.

27. A syringe as recited in claim 23, wherein the chamber is sized such that it can hold only a volume ranging from about m about 0.25 ml to about 0.3 ml.

28. A syringe as recited in claim 23, wherein the length of the plunger means relative to the length of the chamber yields a ratio which is no less than about 1.5:1.

29. A syringe as recited in claim 23, wherein the length of the plunger means relative to the length of the chamber yields a ratio which is no less than about 1.8:1.

30. A syringe as recited in claim 23, wherein the length of the plunger means relative to the length of the chamber yields a ratio which is about 2:1.

31. A syringe as recited in claim 23, wherein the plunger means has a gasket positioned at the distal lead en d of the plunger means.

32. A syringe as recited in claim 23, wherein the barrel has an exit tube extending integrally from the bottom end of the barrel, and wherein the barrel and the plunger means are configured for ventless delivery of a composition out of the chamber through the exit port and into a channel of the exit tube.

33. A syringe for dispensing a composition, the syringe comprising:
   (a) a hollow elongated barrel having:
      a sidewall extending between a top grasping end and an opposing bottom end, the sidewall having an interior surface defining a chamber for holding a composition,
      the barrel having an opening at the top grasping end for accessing the chamber and having an exit port at the bottom end for enabling the composition to exit the chamber, and
      a grasping handle extending perpendicularly and radially from the sidewall at the proximal grasping end of the barrel;
   (b) a plunger positioned within the chamber of the barrel to advance the composition positioned within the barrel through the exit port at the bottom end of the barrel, wherein the plunger has a distal lead end opposite from a proximal pushing end,
      wherein length of the plunger relative to the length of the chamber yields a ration which is no less than about 1.5:1.

34. A syringe for dispensing a composition, the syringe comprising:
   (a) a hollow elongated barrel having:
      a sidewall extending between a top grasping end and an opposing bottom end, the sidewall having an interior surface defining a chamber for holding a composition,
      the barrel having an opening at the top grasping end for accessing the chamber and having an exit port at the bottom end for enabling the composition to exit the chamber, and
      means for grasping the barrel such that a user's fingers can grasp the barrel, the grasping means being located at the proximal grasping end of the barrel;
   (b) plunger means for advancing the composition positioned within the barrel through the exit port at the bottom end of the barrel, the plunger means having a length that is at least twice that of the chamber of the barrel such that when the plunger means is fully advanced within the chamber a portion of the plunger extends out of the chamber with a length that is at least equal to that of the chamber.

35. A syringe as recited in claim 34, wherein the means for grasping the barrel is a grasping handle.

36. A syringe as recited in claim 34, wherein the chamber is sized such that it can hold only sufficient composition for use in a single dental restorative procedure.

37. A syringe as recited in claim 34, wherein the chamber is sized such that it can hold only a volume ranging from about m about 0.2 ml to about 0.6 ml.

38. A syringe as recited in claim 34, wherein the chamber is sized such that it can hold only a volume ranging from about m about 0.25 ml to about 0.3 ml.

39. A syringe as recited in claim 34, wherein the plunger means has a gasket positioned at the distal lead end of the plunger means.

40. A syringe as recited in claim 34, wherein the barrel has an exit tube extending integrally from the bottom end of the barrel, and wherein the barrel and the plunger means are configured for ventless delivery of a composition out of the chamber through the exit port and into a channel of the exit tube.

41. A syringe for dispensing a composition, the syringe comprising:
   (a) a hollow elongated barrel having:
      a sidewall extending between a top grasping end and an opposing bottom end, the sidewall having an interior surface defining a chamber for holding a composition,
      the barrel having an opening at the top grasping end for accessing the chamber and having an exit port at the bottom end for enabling the composition to exit the chamber, and
      a grasping handle extending perpendicularly and radially from the sidewall at the proximal grasping end of the barrel;
   (b) a plunger positioned within the chamber of the barrel to advance the composition positioned within the barrel through the exit port at the bottom end of the barrel, the plunger having a length that is at least twice that of the chamber of the barrel such that when the plunger is fully advanced within the chamber a portion of the plunger extends out of the chamber with a length that is at least equal to that of the chamber.

* * * * *

UNITED STATES PATENT AND TRADEMARK OFFICE
CERTIFICATE OF CORRECTION

PATENT NO. : 6,283,946 B1
DATED : September 4, 2001
INVENTOR(S) : Dan E. Fischer It is certified that error appears in the above-identified patent and that said Letters Patent is hereby corrected as shown below:

Column 2,
Line 59, after "which the" change "practioner" to -- practitioner --

Column 4,
Line 65, before "For example" change "affect" to -- effect --

Column 5,
Line 12, after "Syringe" change "10"" to -- 10'" --
Line 12, after "17." change "FIGS." to -- FIG. --
Lines 54, 59 and 64, after "a" change "practioner" to -- practitioner --

Column 6,
Line 10, after "of the" change "users" to -- user's --
Line 15, after "having an" delete [a]
Line 58, after "amount" and before "effort" insert -- of --
Line 63, after "particularly" change "usefull" to -- useful --

Column 8,
Line 66, after "that a" change "user s" to -- user's --

Column 11,
Line 13, after "manner" and "the user" insert -- that --
Line 37, after "dental" change "practioner" to -- practitioner --
Line 39, after "to the" change "resistant" to -- resistance --
Line 41, after "typically" change "strains" to -- strain --
Line 42, after "becomes" change "to" to -- too --
Line 57, after "amount" and before "effort" insert -- of --

Column 12,
Line 34, after "chamber" and before "hold" insert -- to --
Line 65, after "length of" and before "chamber" insert -- the --

UNITED STATES PATENT AND TRADEMARK OFFICE
CERTIFICATE OF CORRECTION

PATENT NO. : 6,283,946 B1
DATED : September 4, 2001
INVENTOR(S) : Dan E. Fischer It is certified that error appears in the above-identified patent and that said Letters Patent is hereby corrected as shown below:

Column 13,
Line 57, after "at 172." change "Dunng" to -- During --

Column 15,
Line 20, after "barrel" change "her" to -- further --

Column 16,
Line 42, after "deposited such" and before "the" -- that --

Column 17,
Line 20, after "with the" change "users" to -- user's --
Line 49, after "such" and before "the" insert -- that --

Column 18,
Lines 64 and 67, after "about" delete [m about]

Column 19,
Line 11, after "lead" change "en d" to -- end --

Column 20,
Lines 17 and 20, after "about" delete [m about]

Signed and Sealed this

Second Day of July, 2002

Attest:

JAMES E. ROGAN
Attesting Officer    Director of the United States Patent and Trademark Office